US010830738B2

United States Patent
Mziray et al.

(10) Patent No.: US 10,830,738 B2
(45) Date of Patent: Nov. 10, 2020

(54) ULTRASENSITIVE HIGH Q-FACTOR AT-CUT-QUARTZ CRYSTAL MICROBALANCE FEMTOGRAM MASS SENSOR

(71) Applicant: University of Alberta, Edmonton (CA)

(72) Inventors: Selemani Seif Mziray, Edmonton (CA); Thomas Thundat, Edmonton (CA); Kenneth Cadien, Edmonton (CA)

(*) Notice: Subject to any disclaimer, the term of this patent is extended or adjusted under 35 U.S.C. 154(b) by 166 days.

(21) Appl. No.: 15/810,348

(22) Filed: Nov. 13, 2017

(65) Prior Publication Data

US 2018/0143167 A1    May 24, 2018

Related U.S. Application Data

(60) Provisional application No. 62/421,553, filed on Nov. 14, 2016.

(51) Int. Cl.
*G01N 29/24* (2006.01)
*G01N 29/02* (2006.01)
(Continued)

(52) U.S. Cl.
CPC ........... *G01N 29/2443* (2013.01); *C12Q 1/04* (2013.01); *G01N 29/022* (2013.01);
(Continued)

(58) Field of Classification Search
USPC .............................................. 73/61.49, 61.79
See application file for complete search history.

(56) References Cited

U.S. PATENT DOCUMENTS 2,095,376 A * 10/1937 Bechmann ............. H03H 9/131
  310/364
3,478,573 A * 11/1969 King, Jr. ................. H05B 3/26
  73/24.04
(Continued)

FOREIGN PATENT DOCUMENTS

CN    102967521 A    3/2013
CN    102967522 B  * 11/2014

OTHER PUBLICATIONS

Allan, D.W., "Statistics of Atomic Frequency Standards", Proceedings of the IEEE, Feb. 1966, pp. 221-230, vol. 54, Issue 2.
(Continued)

*Primary Examiner* — Daniel S Larkin
(74) *Attorney, Agent, or Firm* — Blue Filament Law PLLC

(57) ABSTRACT

A device for detecting environmental contaminants, diseases, and acute medical conditions related to heart failure identifies pathogens or troponins before infection or damage to heart muscles using an ultrasensitive high Q-factor AT-cut quartz crystal microbalance (QCM) that can measure from a single pg to a single fg. The device has a set of five disks of a QCM with a 10 mm diameter and a full coated bottom electrode, with an upper electrode with a center dot with different diameters labelled as 1 mm, 2 mm, 3 mm, 4 mm, and 5 mm. The full coating denoting an electrically continuous thickness of at last one monolayer. Measured parameters from the five disks include Q-factors, impedance, dissipation factors (D) and frequency shift ($\Delta f$). Q-factors are used to calculate the Allman deviation $\sigma(\tau)$ and measured frequencies are converted to mass sensitivity using the Sauerbrey mass sensitivity coefficient (K).

14 Claims, 15 Drawing Sheets

(51) Int. Cl.
*G01N 29/036* (2006.01)
*G01N 33/543* (2006.01)
*G01N 29/22* (2006.01)
*C12Q 1/04* (2006.01)

(52) U.S. Cl.
CPC ......... *G01N 29/036* (2013.01); *G01N 29/222* (2013.01); *G01N 33/5438* (2013.01); *G01N 33/54373* (2013.01); *G01N 2291/0255* (2013.01); *G01N 2291/0256* (2013.01); *G01N 2291/0426* (2013.01)

(56) References Cited

U.S. PATENT DOCUMENTS

| | | | |
|---|---|---|---|
| 6,722,200 | B2 | 4/2004 | Roukes et al. |
| 7,869,013 | B2 | 1/2011 | Wang et al. |
| 8,215,171 | B1 | 7/2012 | Smith et al. |
| 8,486,721 | B2* | 7/2013 | Campbell ........ G01N 33/54326 436/526 |
| 8,667,845 | B2* | 3/2014 | Defay .................. G01N 29/022 73/592 |
| 9,121,771 | B2 | 9/2015 | Tadigadapa et al. |
| 2009/0038859 | A1 | 2/2009 | Itoh |
| 2009/0145233 | A1 | 6/2009 | Eklund et al. |
| 2009/0229980 | A1 | 9/2009 | Hughes et al. |
| 2011/0064615 | A1* | 3/2011 | Watanabe ................. G01N 5/02 422/69 |
| 2013/0276176 | A1* | 10/2013 | Polesel-Maris ........ B82Y 35/00 850/40 |
| 2016/0033341 | A1 | 2/2016 | Tadigadapa et al. |
| 2016/0061777 | A1 | 3/2016 | Takasu |

OTHER PUBLICATIONS

Cummins, B. et al., "Cardiac-specific troponin-I radioimmunoassay in the diagnosis of acute myocardial infarction", American Heart Journal, Jun. 1987, pp. 1333-1344, vol. 113, Issue 6; DOI: https://doi.org/10.1016/0002-8703(87) 90645-4.

Hook, F. et al., Energy Dissipation Kinetics for Protein and Antibody-Antigen Adsorption under Shear Oscillation on a Quartz Crystal Microbalance, Langmuir, Jan. 28, 1998, pp. 729-734, vol. 14, Issue 4, © 1998 American Chemical Society; DOI: 10.1021/la970815u.

O'Sullivan, C.K. et al., "Commercial quartz crystal microbalances—theory and applications", Biosensors and Bioelectronics, Dec. 1999, pp. 663-670, vol. 14, Issues 8-9, © 1999 Elsevier Science S.A; DOI: 10.1016/S0956-5663(99)00040-8.

Lavrik, N.V. et al., "Femtogram mass detection using photothermally actuated nanomechanical resonators", Applied Physics Letters, Apr. 21, 2003, pp. 2697-2699, vol. 82, Issue 16, © 2003 American Institute of Physics; DOI: 10.1063/1.1569050.

Lin, Y. et al., "Glucose Biosensors Based on Carbon Nanotube Nanoelectrode Ensembles", Nano Letters, Feb. 2004, pp. 191-195, vol. 4, Issue 2, © 2004 American Chemical Society; DOI: 10.1021/nl0347233.

Ilic, B. et al., "Attogram detection using nanoelectromechanical oscillators", Journal of Applied Physics, Apr. 1, 2004, pp. 3694-3703, vol. 95, Issue 7, © 2004 American Institute of Physics; DOI: 10.1063/1.1650542.

Ekinci, K.L. et al., "Ultrasensitive nanoelectromechanical mass detection", Applied Physics Letters, May 31, 2004, pp. 4469-4471, vol. 84, Issue 22, © 2004 American Institute of Physics; DOI: 10.1063/1.1755417.

Rodriguez-Pardo, L. et al., "Sensitivity, Noise, and Resolution in QCM Sensors in Liquid Media", IEEE Sensors Journal, Dec. 2005, pp. 1251-1257, vol. 5, Issue 6, © 2005 IEEE; DOI: 10.1109/JSEN.2005.859257.

Christenson, R.H. et al., "Biomarkers of Myocardial Necrosis", Cardiovascular Biomarkers: Pathophysiology and Disease Management, Editor: Morrow, D.A., 2006, pp. 3-25, © 2006 Humana Press; DOI: 10.1007/978-1-59745-051-5_1.

Yang, Y.T. et al., "Zeptogram-Scale Nanomechanical Mass Sensing", Nano Letters, Apr. 2006 (Published Online: Mar. 15, 2006), pp. 583-586, vol. 6, Issue 4, © Copyright 2006 by the American Chemical Society; DOI: 10.1021/hl052134m.

Villarroya, Maria et al., "System on chip mass sensor based on polysilicon cantilevers arrays for multiple detection", Sensors and Actuators A, Nov. 2006 (Published Online: May 15, 2006), pp. 154-164, vol. 132, Issue 1, © 2006 Elsevier B.V.; DOI: 10.1016/j.sna.2006.04.002.

Petrovick, M.S. et al., "Rapid Sensors for Biological-Agent Identification", Lincoln Laboratory Journal, 2007, pp. 63-84, vol. 17, Issue 1; https://www.ll.mit.edu/publications/journal/pdf/vol17_no1/17_1_3Petrovick.pdf.

Jackson, M.J. and Ahmed, W. (Editors), "Applications of Carbon Nanotubes in Bio-Nanotechnology", Surface Engineered Surgical Tools and Medical Devices, Chapter 12, 2007, © Springer Science+Business Media, LLC 2007; DOI: 10.1007/978-0-387-27028-9_12.

Moure, M.J. et al., "An FPGA-based system for the measurement of frequency noise and resolution of QCM sensors", Latin American Applied Research, Jan. 2007, pp. 25-30, vol. 37, Issue 1; https://www.researchgate.net/publication/228632600_An_FPGA-based_system_for_the_measurement_of_frequency_noise_and_resolution_of_QCM_sensors.

Veetil, J.V. et al., "Development of Immunosensors Using Carbon Nanotubes", Biotechnol. Prog., May-Jun. 2007 :Published Online: Apr. 26, 2007), pp. 517-531, vol. 23, Issue 3; © 2007 American Chemical Society and American Institute of Chemical Engineers; DOI: 10.1021/bp0602395.

Cooper, M.A. et al., "A survey of the 2001 to 2005 quartz crystal microbalance biosensor literature: applications of acoustic physics to the analysis of biomolecular interactions", Journal of Molecular Recognition, May-Jun. 2007, pp. 154-184, vol. 20, Issue 3, Copyright © 2007 John Wiley & Sons, Ltd; DOI:10.1002/jmr.826.

Dohn, S. et al., "Mass and position determination of attached particles on cantilever based mass sensors", Review of Scientific Instruments, Oct. 2007, pp. 103303-1-103303-3, vol. 78, Issue 10, © 2007 American Institute of Physics; DOI: 10.1063/1.2804074.

Tate, J.R., "Troponin revisited 2008: assay performance", Clin. Chem. Lab. Med., 2008, pp. 1489-1500, vol. 46, Issue 11, © 2008 by Walter de Gruyter; DOI 10.1515/CCLM2008.292.

Akita, S. et al., "Carbon Nanotube Mechanical Resonators for Mass Sensing", Sensors and Materials, 2009, pp. 339-349, vol. 21, Issue 7; http://myukk.org/SM2017/sm_pdf/SM774.pdf.

Barton, R.A. et al., Resonant Mass Sensors Containing Nanofluidics, MEMS & NEMS Research, 2 pages, Created by Phil Waggoner © 2009; Retrieved from the Internet on May 21, 2018; http://www.hgc.cornell.edu/research/nems/fluidnems.htm.

Conroy, P.J. et al., "Antibody production, design and use for biosensor-based applications", Seminars in Cell & Developmental Biology, Feb. 2009, pp. 10-26, vol. 20, Issue 1, © 2009 Published by Elsevier Ltd.; DOI: 10.1016/j.semcdb.2009.01.010.

Kurzbuch, D. et al., "A biochip reader using super critical angle fluorescence", Sensors and Actuators B: Chemical, Mar. 2009, pp. 1-6, vol. 137, Issue 1, © 2009 Elsevier B.V.; DOI: 10.1016/j.snb.2008.12.057.

Keller, T. et al., "Sensitive Troponin I Assay in Early Diagnosis of Acute Myocardial Infarction", The New England Journal of Medicine, Aug. 27, 2009, pp. 868-877, vol. 361, Issue 9, Copyright © 2009 Massachusetts Medical Society; DOI: 10.1056/NEJMoa0903515.

Dimov, I.K. et al., "Stand-alone self-powered integrated microfluidic blood analysis system (SIMBAS)", Lab on a Chip, Mar. 2011, pp. 845-850, vol. 11, Issue 5, © The Royal Society of Chemistry 2011; DOI: 10.1039/c0lc00403k.

Hill, D. et al., "Novel disposable biochip platform employing supercritical angle fluorescence for enhanced fluorescence collection", Biomed. Microdevices, Aug. 2011 (Published Online: May 11, 2011), pp. 759-767, vol. 13, Issue 4, © Springer Science+Business Media, LLC 2011; DOI: 10.1007/s10544-011-9546-2.

Ahammad, A.J. et al., "Electrochemical Detection of Cardiac Biomarker Troponin I at Gold Nanoparticle-Modified ITO Electrode by Using Open Circuit Potential", Int. J. Electrochem. Sci., Jun. 2011, pp. 1906-1916, vol. 6, © 2011 by ESG; http://www.electrochemsci.org/papers/vol6/6061906.pdf.

(56) References Cited

OTHER PUBLICATIONS

Garcia-Martinez, G. et al., "Development of a Mass Sensitive Quartz Crystal Microbalance (QCM)-Based DNA Biosensor Using a 50 MHz Electronic Oscillator Circuit", Sensors, Aug. 3, 2011, pp. 7656-7664, vol. 11, © 2011 by the authors; licensee MDPI, Basel, Switzerland; DOI: 10.3390/s110807656.

Becker, B. et al., "A survey of the 2006-2009 quartz crystal microbalance biosensor literature", J. Mol. Recognit., Sep.-Oct. 2011, pp. 754-787, vol. 24, Issue 5, Copyright © 2011 John Wiley & Sons, Ltd.; DOI: 10.1002/jmr.1117.

Diercks, D.B. et al., "Diagnostic accuracy of a point-of-care troponin I assay for acute myocardial infarction within 3 hours after presentation in early presenters to the emergency department with chest pain", American Heart Journal, Jan. 2012, pp. 74-80.e4, vol. 163, Issue 1, © 2012, Mosby, Inc.; DOI: 10.1016/j.ahj.2011.09.028; https://www.ahjonline.com/article/S0002-8703(11)00721-6/fulltext.

Conroy, P.J. et al., "Cardiac troponin I: a case study in rational antibody design for human diagnostics", Protein Engineering, Design & Selection, Jun. 2012 (Published Online: Apr. 16, 2012), pp. 295-305, vol. 25, Issue 6, © The Authors 2012; DOI: 10.1093/protein/gzs018; https://academic.oup.com/peds/article/25/6/295/1481412.

Reichlin, T. et al., "One-Hour Rule-out and Rule-in of Acute Myocardial Infarction Using High-Sensitivity Cardiac Troponin T", Arch. Intern. Med., Sep. 10, 2012, pp. 1211-1218, vol. 172, Issue 16, © 2012 American Medical Association; DOI: 10.1001/archinternmed.2012.3698.

Speight, R.E. et al., "A Survey of the 2010 Quartz Crystal Microbalance Literature", J. Mol. Recognit., Sep. 2012, pp. 451-473, vol. 25, Issue 9, Copyright © 2012 John Wiley & Sons, Ltd.; DOI: 10.1002/jmr.2209.

Faegh, S. et al., "A Self-Sensing Piezoelectric MicroCantilever Biosensor for Detection of Ultrasmall Adsorbed Masses: Theory and Experiments", Sensors, May 10, 2013, pp. 6089-6108, vol. 13, Issue 5, © 2013 by the authors; licensee MDPI, Basel, Switzerland; DOI: 10.3390/s130506089; http://www.mdpi.com/1424-8220/13/5/6089.

Sharma, A. et al., "Efficiency of Airborne Sample Analysis Platform (ASAP) bioaerosol sampler for pathogen detection", Frontiers in Microbiology, May 27, 2015, 7 pages, vol. 6, Article 512; DOI: 10.3389/fmicb.2015.00512; https://www.ncbi.nlm.nih.gov/pmc/articles/PMC4444837/.

Ho, C. et al., "Point-of-Care Cardiac Troponin Testing in Patients With Symptoms Suggestive of Acute Coronary Syndrome—Project Protocol", Canadian Agency for Drugs and Technologies in Health (CADTH), Jun. 2015, 20 pages, CADTH Optimal Use Report, vol. 5, Issue 1a, © 2015 CADTH, Retrieved from Internet on May 21, 2018; https://www.cadth.ca/sites/default/files/pdf/OP0519_PoC_Troponin_Protocol_June%202015.pdf.

Jo, H. et al., "Electrochemical Aptasensor of Cardiac Troponin I for the Early Diagnosis of Acute Myocardial infarction", Analytical Chemistry, Oct. 6, 2015 (Published Online: Sep. 30, 2015), pp. 9869-9875, vol. 87, Issue 19, © 2015 American Chemical Society; DOI: 10.1021/acs.analchem.5b02312.

Ho, C. et al., "Point-of-Care Troponin Testing in Patients With Symptoms Suggestive of Acute Coronary Syndrome: A Health Technology Assessment", Canadian Agency for Drugs and Technologies in Health (CADTH), Mar. 2016, 144 pages, CADTH Optimal Use Report, vol. 5, Issue 1b, © 2016 CADTH, Retrieved from Internet on May 21, 2018; https://www.ncbi.nlm.nih.gov/books/NBK362823/.

\* cited by examiner

Cursors Readout:

Left Cursor:
x: 0 s
y: 1.6939999903322 MHz

Right Cursor:
x: 9.0909091 35909 s
y: 1.6939999905286 MHz

Between Cursors:
dx: 9.0909091 35909 s
dy: 2.065832726657 mHz
dn: 10 Samples
1/dx: 109.999999455 5 mHz
dy/dx:
dx/dy:

Statistic Parameters :
Min: 1.6939999901784 MHz
Max: 1.6939999906187 MHz
Delta: 4.4035273895 mHz
Mean: 1.6939999903709 MHz
S.Dev: 952.4735323465 uHz
A.Dev: 1.0226875704 15 mHz

FIG. 9B

ULTRASENSITIVE HIGH Q-FACTOR AT-CUT-QUARTZ CRYSTAL MICROBALANCE FEMTOGRAM MASS SENSOR

RELATED APPLICATION

This application claims priority benefit of U.S. Provisional Application Ser. No. 62/421,553 filed Nov. 14, 2016; the contents of which are hereby incorporated by reference.

TECHNICAL FIELD

The present invention generally relates to the field of biosensors, and more specifically to an ultrasensitive high Q-factor AT-cut quartz crystal microbalance (QCM) femtograms (fg or $10^{-15}$ g) mass sensor.

BACKGROUND

One of the current technological challenges in diagnostic medical equipment is to develop simple and cost-effective sensor systems to detect a mass in fg regime, and therefore being capable of detecting troponins in the human blood serum and airborne pathogens, in less than ten seconds before infection. Although antigen-antibody selectivity is possible on a special assay developed on the surface of the sensor; interference from blood electrolytes, hormones, molecules and cells remains a big challenge which may need a separation technique to isolate a specific virus, a specific bactrerium, or a single molecule from the whole blood or ambient air.

The airborne parthogens can be used not only in the battle field as a weapon to kill millions of people without warning; but also, as an infectious disease in agricultural and food industry sectors. For examples, small pox, anthrax, tuberculosis, severe acute respiratory syndrome (SARS) virus, and foot and mouth disease are some of the known driving needs for improved biosensors with increased sensitivity to detect fg scale in less than ten seconds. Other diseases such as heart failure caused by acute myocardial infraction (AMI) could also benefit from a sensor which is sensitive enough to detect troponin level in the fg regime in real time before a stroke or heart failure.

While many inventions with picograms (pg or $10^{-12}$ g/cm$^2$) to fg mass resolution have been published, the technology to measure beyond pg scale has not yet been developed as a working mass sensor system. Extension of this technology beyond pg could open up new business opportunities globally, in material sciences, life sciences, and in medical and diagnostic point of care.

Ultrasensitive mass sensing devices, such as nanoelectromechanical systems (NEMS) and micro cantilevers that include a family of QCM, and carbon nanotube (CNT), have shown a higher mass sensitivity and high throughput analysis capable of detecting a specific bioreceptor to which a target antibody or antigen binds. Upon binding of antigen/antibody targets on the sensor, the change in mass is related to a measurable output frequency in relation to the binding species such as a single cell, a molecule, a virus, a troponin, or a bacterium. These micro-organisms are in the pg to fg scale weight regime and can easily be detected by matching their masses with frequency change using devices with high mass resolutions in the pg to fg regimes. Although many patents based on CNT, micro-cantilevers, MEMS, NEMS and QCM have claimed to measure pg, fg, attogram ($10^{-18}$ g or ag), and zeptogram (zg or $10^{-21}$ g), the technology to measure mass beyond pg in real time does not exist due to difficulty in fabrication and reproduction of the same devices and results.

CANARY/PANTHER is a popular technology currently used for detection of airborne pathogens in site buildings, emergency response, and rapid screening of disease outbreak in public areas. CANARY/PANTHER technology contains both optical and signal transduction systems used to simultaneously to detect airborne pathogens in real time. CANARY/PANTHER pathogen detection sensors detect less than fifty colony-forming units (cfus) of the pathogen in one to ten minutes, depending on the pathogen being detected, neglecting sample processing time from micro handling devices, and therefore the sample preparation. Furthermore, considering the time taken to capture the pathogens from aerosol chamber to micro centrifuge, and then to the photodetector, the CANARY/PANTHER technology seems more time consuming as it needs sample preparation and reprocessing. Thus, the challenges with this technique are primarily sample preparation involving the use of micro-centrifuges, B-cells, or micro-air handling devices. CANARY/PANTHER technology is also burdened by the long-term storage of refrigerated B-cell reagents which are ineffective in other applications.

Mass Spectroscopy (MS) is another technique used for pathogen detection, but requires several days or weeks for results and faces challenges such as miniaturization (maintaining effectiveness), preprocessing samples, introducing samples to the MS chamber, and interpreting spectral signals. Therefore, results using mass spectroscopy are not available in near real-time that are critical in the avoidance of illness, outbreaks, or illicit attacks.

A QCM mass sensor is a simple, cost-effective, high-resolution mass-sensing technique used to study properties of monolayer surfaces deposited on quartz wafers such as molecules, bacteria, antibody-antigen interaction, single cells, proteins, and thin films of polymers. A QCM sensors use a phenomenon in which when the mass of the electrode increases due to corrosion or mass deposited, the oscillation frequency of the quartz oscillator is reduced according to the amount of corrosion. The QCM sensor is capable of detecting a change in oscillation frequency of a quartz oscillator with a very high degree of sensitivity, and is capable of performing measurement in a short period of time compared to that of a sensor that uses other measuring methods, such as a coupon method. Therefore QCM sensors are often adopted as an environment measuring device. QCM sensors are comparatively inexpensive, easy to fabricate and manufacture, and commercially available in the market. Commercial QCM sensors have the ability to measure mass to approximately $1 \times 10^{-9}$ to $10^{-12}$ g/cm$^2$.

QCM sensors are also capable of measuring mass and energy dissipation properties of surface functionalized biomaterials while simultaneously carrying out electrochemistry studies on solution species. Sauerbrey was the first to recognize the potential usefulness of the QCM technology and demonstrated the mass sensitivity nature towards frequency changes at the surface of QCM electrodes. Sauerbrey derived the equation which relates the mass change per unit area at the QCM electrode surface to the observed change in oscillation frequency of the crystal as shown in the following equation:

If the expression: $K = 2 \ast f^2 / \sqrt{\rho\mu} = 2.26 \ast 10^{-6} f^2$ Hz·cm$^2$/g, where K is the mass sensitivity coefficient, $\rho = 2.648$ g/cm$^3$, is the density of quartz crystal, and $\mu = 2.947 \ast 10^{11}$ g/cm·s$^2$, is the shear modulus of quartz crystal. By using the Sauerbrey's mass sensitivity coefficient, it has been shown that it is possible to use AT-cut QCM to measure mass of thin film functionalized on quartz disk to 2.7 fg/cm$^2$ (L. Rodriguez-Pardo, J. F. Rodriguez, C. Gabrielli, H. Perrot. Sensitivity, noise, and resolution in QCM sensors in liquid media. IEEE Sensors Journal. 5, 6 (2005)).

After Sauerbrey derived an important equation which relates mass of a substrate added on a quartz disk to frequency shift, Allan was the next to derive an equation which represented frequency stability and noise arising from the driving oscillator circuit in the time domain in less than ten seconds (M. J. Moure, P. Rodiz, D. Valdes, L. F. Rodriguez-Padro, and J. Farina. An FPGA based system for the measurement of frequency noise and resolution of QCM sensors. Latin American Applied Research. 37, 30 (2007)).

The Institute of Electrical and Electronics Engineers (IEEE) has recognized Allan's equation and called it the Allan variance (IEEE Std. 1139, 1999) with the expression: $\sigma=(1*10^{-7})/Q$, where $\sigma$ is the Allan variance and Q is the Q-factor of an AT-cut quartz disk. In embodiments of this invention, both Sauerbrey and Allan deviation equation are applied, and it has been shown that if the mass sensitivity coefficient of AT-cut quartz disk is known, it is possible to estimate mass resolution using as measured Q-factors. Since the Allan deviation $\sigma(\tau)$, can be estimated using $\sigma=10^{-7}/Q$; then, the detection limit $\Delta f(\tau)$ can be calculated using the equation, $\sigma(\tau)*f(\tau)=\Delta f(\tau)$. The mass resolution on the surface of the active electrode area can be calculated by taking the ratio of detection limit $\Delta f(\tau)$ to mass sensitivity coefficient (K). It has also been reported in the literature that the typical absolute dissipation ($\Delta D$) values of crystals oscillating in air and water are about $1*10^{-5}$ and $3.5*10^{-4}$, respectively, the $\Delta D$ reported in literature upon exchange of the protein on a gold electrode is approximately $1*10^{-6}$ (F. Hook, M. Rodahl, P. Brzezinski, and B. Kasemo. Energy dissipation kinetics for protein and antibody-antigen adsorption under shear oscillation on a quartz crystal microbalance. Langmuir 14, (2998), 729-734).

Acute myocardial infarction (AMI) is one of the leading global causes of death, however, AMI can still be difficult to diagnose in patients. In 2014 the globally representative U.S. market for cardiac biomarker diagnostics was $551 million (Analysis of the cardiac biomarker diagnostics market, Frost & Sullivan, September 2015), increasing with an annual growth rate of approximately 5%. The market for cardiac biomarker diagnostics is split relatively evenly between lab based heart failure tests and point of care (POC) tests, but POC tests are cannibalizing the lab based market, implying a greater growth rate than the broader market. Troponin assays are considered to be the gold standard for diagnosing AMI and could grow to encompass much of the POC market with a more sensitive and less expensive option.

In the continuum of acute coronary syndrome (ACS), cardiac biomarkers now play a key role in the diagnosis, prognosis, and risk stratification of patients. The cardiac troponins (cTn) are part of the regulatory complex involved in cardiac striated muscle contraction and include Troponin I (cTnI), Troponin C (TnC), and Troponin T (cTnT) subunits. The cTnI is the current gold standard biochemical marker for definitive diagnosis of AMI. In the late 1990s, the epitopes such as cTnI and later cTnT assays were able to detect troponin from patient's blood at ng/ml levels. In practice, these assays allowed for a reliable detection of troponins only three to six hours after the onset of chest pain as markers of AMI. In contrast, modern high-sensitivity assays, whose detection limit is pg/ml rather than ng/ml, have made it possible to indicate a possible AMI patient within the first one to three hours after a troponin generating episode. The current generation of commercially available high-sensitivity assays is about 1000 times more sensitive (10 pg/ml vs. 10 ng/ml) than the first cTnI and cTnT assay described in 1987. Higher sensitivity helps to register even minor cardiac events resulting in necrosis or apoptosis of myocardial tissue.

POC tests can drastically increase patients' chances of survival because they can be administered much more quickly than the lab tests. A report prepared by the Canadian Agency for Drugs and Technologies in Health (CADTH) entitled "Point-of-Care cardiac troponin testing in patients with symptoms suggestive of acute coronary syndrome", Jun. 20, 2015 compares annual hospital expenditures related to myocardial infraction (MI) while using POC devices to central laboratories testing in various Canadian health care settings. The CADTH report cited an estimate of 818,847 Canadian emergency room visits were made in 2009 for suspected acute coronary syndrome (ACS), and found that from time of presentation at the emergency department to one year later, the costs per patient, after undergoing standard laboratory testing of cardiac troponin (cTn), ranged from C$2,018 to C$2,186 per patient per year, which included the costs of false-positive hospitalizations. Multiplying the total emergency visits by C$2,018 leads to an estimated annual cost of C$1,652,433,246 to care for patients in the emergency departments with suspected ACS and who undergo laboratory testing for cTn.

Most diagnostic POC devices are limited to picogram sensitivity, failing to detect diseases in their early stages, and they are currently used to detect Myocardial Infraction (MI) to provide results in four to six hours after the incidence of heart failure. Currently, none of the existing POC devices have the ability to monitor the rise and fall of troponin level of a normal patient who will experience MI in a few months. POC devices that are able to detect troponin level below single pg levels could save billions of Canadian dollars and save the lives of many people by detecting the ACS, MI, and AMI, before it happens in home settings prior to an actual life-threatening MI (heart attack) or stroke and a required emergency room admittance.

Therefore, the use of point of care (POC) devices requires improved analytical sensitivity to detect the lower clinically relevant cTn concentrations. Research into increasingly sophisticated POC platforms potentially permits the development of more advanced systems using novel signal transduction platforms, modified surfaces, microfluidic and detection systems. The trend towards miniaturization (nano and micro) complicates the process in terms of the ancillary components required but also introduces challenges for the type and quality of antibody developed for such applications. Therefore, the introduction of nanoscale mass sensing devices such as QCM, micro-cantilevers, carbon nanotube (CBN), and MEMS with higher mass sensitivity and detection limit of fewer than ten seconds may provide a solution to the current problems of using CANARY/PANTHER and MS techniques. These devices depend only on the frequency shift and no photodetector or microcentrifuge is needed; because the change in frequency is directly proportional to the mass of antigen, antibody, or equivalent to that of a bacterium or a virus. Other devices which could also be used are micro-cantilevers and CBN with higher mass resolutions in the range from sub-picograms ($10^{-12}$ g), femtograms ($10^{-15}$ g), attograms ($10^{-18}$ g), and zeptograms ($10^{-21}$ g).

Nevertheless, the difficulty in the CBN and micro-cantilevers manipulation process complicates the fabrication of the nano-scale mass sensors; making it difficult to develop and commercialize high sensitive mass sensor systems. Among these sensors, the only one which is cheap, easy to fabricate and manufacture, and commercially available in the market, is QCM sensors. Although modification of the electrode configurations of thickness shear mode (TSM) resonator devices have been reported to exhibit uniformity of mass sensitivity and high-frequency stability, TSM resonator devices are capable of accurately measuring mass down to nanogram (ng) or pictogram ($10^{-12}$ g). As such, and as disclosed by Smith et al (V. Smith. R. Bhethanabotla, A. J. Richardson. Uniform mass sensitivity thickness shear mode quartz resonator, U.S. Pat. No. 8,215,171, Jul. 10, 2012) and Hin (W. Hin. Quartz crystal microbalance (QCM) mass sensor, Patent No. CN 102967521, Apr. 15, 2015); a sensing device with a series of electrodes on an AT-cut quartz has a 20 mm diameter designed to work at 5 MHz, 10 MHz or 11 MHz, yielding different mass sensitivity as the diameter of a ring or center electrode decreased. This prior art showed that smaller electrodes with diameter from 1.5 mm to 8 mm result in more sensitive mass detection within the electrode region of the quartz crystal operated at 5 MHz and $3^{rd}$ and $5^{th}$ overtones. Also, a method for sensing and adding nanotubes to a sensor to improve characteristics such as the Q-factor associated with the sensor has been reported. This is a micromachined 48.535731 MHz quartz crystal resonator in which a thin film of single-walled carbon nanotube (SWNT) has been disclosed with a mass sensitivity of $100*10^{-15}$ g/cm$^2$ in a vacuum. Among these patents and those based on MEMS, micro-cantilevers, and CNT, none of these inventions have been converted to a commercial system to measure mass beyond the pg regime.

Therefore, there is a need for cost-effective and sensitive diagnostic equipment to detect environmental contaminants, diseases, and acute medical conditions before infection and occurrence by detecting and identifying airborne pathogens or troponins for more rapid interventions.

BRIEF DESCRIPTION OF THE DRAWINGS

The present invention is further detailed with respect to the following drawings that are intended to show certain aspects of the present invention, but should not be construed as a limit on the practice of the invention, wherein:

FIG. 9B shows the measurement information associated with the plow of FIG. 9A;

SUMMARY OF THE INVENTION

A sensor includes a quartz substrate with a top side and a bottom side, a center electrode centered on the top side of the quartz substrate, and a ring electrode on the top side surrounding the center electrode, where there is a gap between the ring electrode and the center electrode. The sensor further includes a full electrode on the bottom side.

A method of using a sensor for early detection of infectious diseases and troponins for AMI and airborne pathogens includes forming a sample of blood mixed with a saline solution or a sample of ambient air, and feeding the sample into a microfluidic-controlled by ultrasonic acoustic forces to separate the supplied whole blood sample into suspended particles of antigens, antibodies, electrolytes, cells, bacteria and troponins, or the sampled air into antigens. The method further includes coating the sensor with an antibody or anti-troponin, and supplying the separated whole blood sample, or the sample air antigens to a reflector or a special microchannel crystal window doped with antibodies, to apply the samples to the sensor.

DETAILED DESCRIPTION OF THE INVENTION

Figure 13:
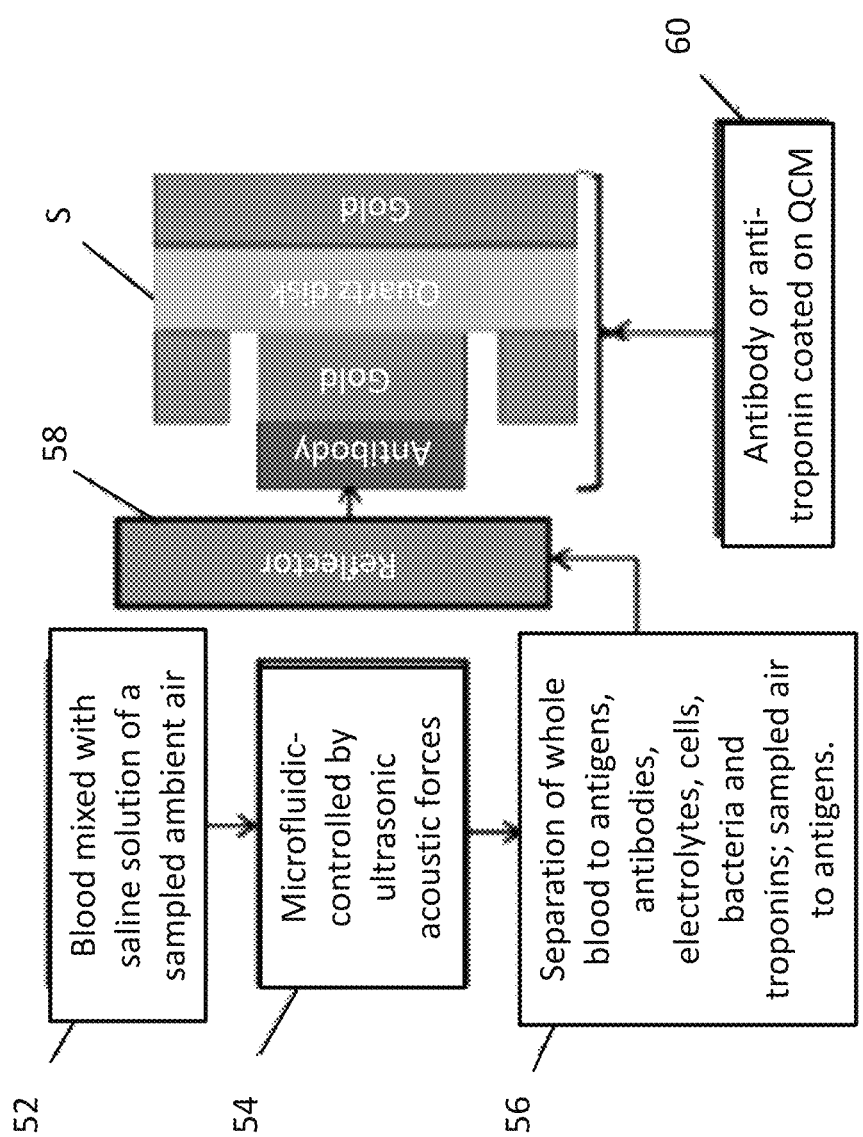
FIG. 13 is the flow chart which shows a set-up for isolating an antigen, antibody, or troponin from the sampled air or whole blood using an ultrasonic acoustic forces separation technique in accordance with embodiments of the invention.

The present invention has utility as a device for cost-effective and sensitive diagnostics to detect environmental contaminants, diseases, and acute medical conditions related to heart failure by identifying pathogens or troponins before infection or damage to heart muscles. Embodiments of the invention include an ultrasensitive high Q-factor AT-cut quartz crystal microbalance (QCM) that can measure from a single pg to a single fg. In specific inventive embodiments, a set of five disks of a QCM has a 10 mm diameter with a full coated bottom electrode, with an upper electrode that has a center dot with different diameters labelled as 1 mm, 2 mm, 3 mm, 4 mm, and 5 mm. The full coating denoting an electrically continuous thickness of at least one monolayer. The measured parameters from the five disks illustratively include Q-factors, impedance, dissipation factors (D) and frequency shift (Δf). The obtained Q-factors were used to calculate the Allan deviation σ(τ) and at the same time, the measured frequencies were converted to mass sensitivity using the Sauerbrey mass sensitivity coefficient (K). The detection limits Δf(τ) were then calculated by multiplying Δf(τ) to f(τ). The mass resolutions in (g/cm$^2$) for all disks were calculated by taking the ratio of Δf(τ) to K. The disk with 2 mm center dot has been found to be more sensitive and can measure to a single fg sensitivity in less than ten seconds and with reproducibility. The inventive disk with 2 mm center electrode was used to design a cost-effective analog box as a compact and portable sensitive biosensor that will fill market gaps not only in early detection of infectious diseases and troponins for AMI and airborne pathogens; but also, in a wide range of research not currently covered by bulk acoustic wave (BAW) biosensors. The ability to integrate embodiments of the analog box having reference immunoassay and built-in immunoassay electronics with field programmable gate array (FPGA) will add additional functionality to MEMS devices in the micro nano technology (MNT) area, whereas, an inventive embodiment of a separation device as shown in FIG. 13 provides the capability to isolate particles of interests from whole blood or ambient air. Embodiments of the inventive disk with a 2 mm center electrode incorporate thin layers of antibody and that of cTnI and later cTnT assays which are able to detect troponins and virus or bacterium in a fg regime (of a single pg to a single fg) in the air and in whole blood faster than any available assays currently in the market. The present invention is amenable to incorporation in other portable devices for blood and air particle separation, where detection is through use of the ultra-sensitive disk with a 2 mm central diameter. Embodiments of the invention may also be incorporated in a wireless device used in home settings, where the client's doctor can have access to intergraded wireless networks that connect the individual clients to the central doctor's office.

Embodiments of the inventive disk are one hundred times more sensitive than the currently used D-QCM technology, and as a result, the disk may be used to probe viscoelastic properties induced by small proteins, such as antibody-antigen interaction, while still maintaining its absolute dissipation factor as $1.2*10^{-7}$ in the air. Furthermore, embodiments of the inventive disk may be used to measure ΔD up to $10^{-8}$, as well as provide new information about thermodynamics, binding, conformational changes, viscoelastic, phase transitions, and kinetics of macromolecular systems at phase boundaries.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Figure 1:
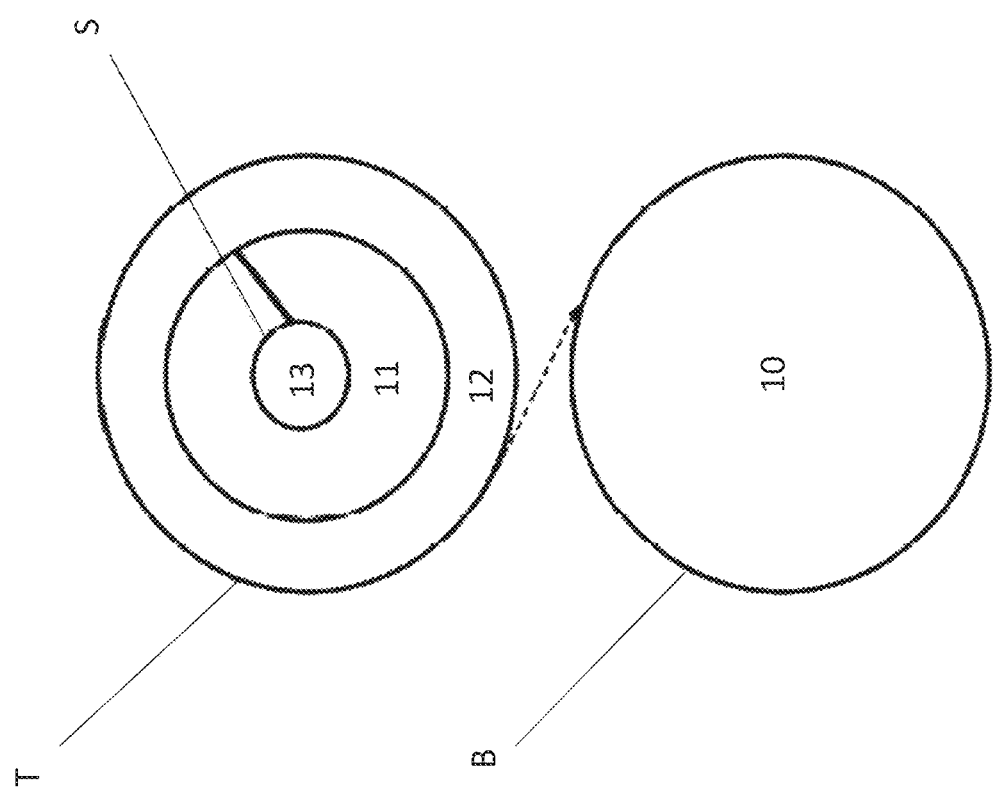
FIG. 1 depicts top and bottom views of a fabricated disk showing an electrode configuration in accordance with embodiments of the invention.

Referring now to the figures, FIG. 1 is a diagram of a top (T) side with a sensitive center dot electrode (S) and bottom (B) view of an embodiment of the ground terminals of the fabricated disks. In a specific embodiment, the disks may be fabricated using sputter deposited gold electrode layers of approximately 300 nm on a chromium adhesion layer of approximately 50 nm. The top side T of the disk has a center electrode 13 separated from a ring electrode 12 by a nap 11. The bottom side B of the quartz, disk is a full electrode 10. In a specific inventive embodiment, a set of five disks of a QCM have a 10 mm diameter with a full coated bottom electrode, with an upper electrode that has a center electrode 13 with different diameters illustratively including 1 mm, 2 mm, 3 mm, 4 mm, and 5 mm.

Figure 2:
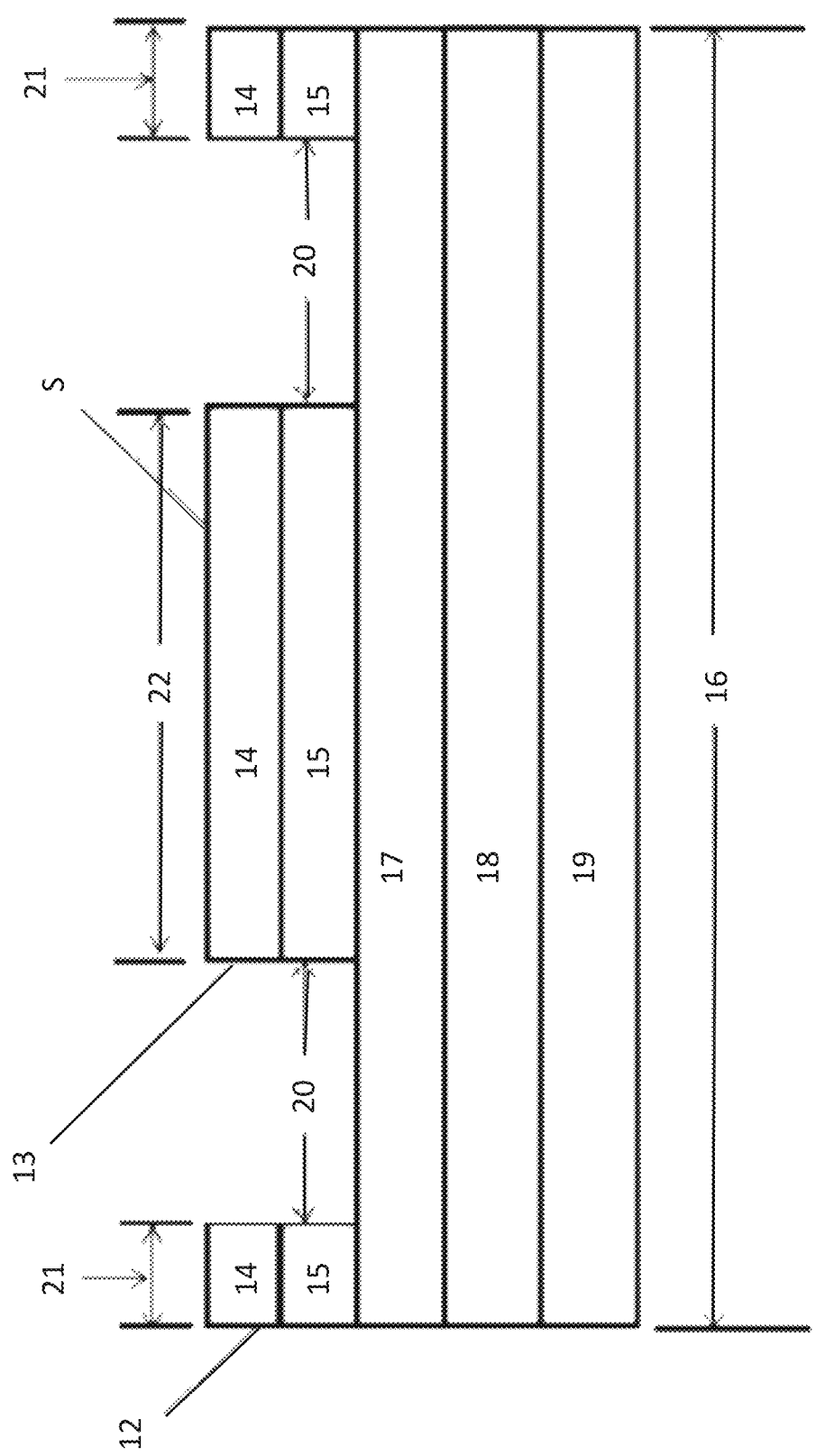
FIG. 2 depicts a side view of the fabricated disks showing layers of chromium adhesive, a gold electrode, and quartz disks in accordance with embodiments of the invention.

FIG. 2 is a side view of a multi layered AT-cut quartz disk. The center dot electrode 13 has both a gold (Au) layer 14 and chromium (Cr) adhesive layer 15 with a diameter represented by arrow 22. The ring electrode 12 is also a gold layer 14 deposited on the chromium adhesive layer 15, where the width of the ring electrode 12 is represented by arrow 21. The width of the gap 11 is shown by arrow 20 between the center electrode 13 and the outer ring electrode 12. When the center dot electrode 13 is 1 mm, 2 mm, 3 mm, 4 mm, and 5 mm, the width of the gap is 2.5 mm, 2 mm, 1.5 mm, 1 mm, and 0.5 mm, respectively. At the bottom B of the blank quartz disk 17, there are two more layers, the chromium adhesive layer 18 and the gold electrode layer 19. The diameter of the full coated electrode on the bottom B of the quartz disk 17 is 10 mm represented by arrow 16.

It is appreciated that AT-cut quartz may have an anisotropic shape and not just circular as shown in FIGS. 1 and 2. It is also appreciated that the thicknesses of the applied gold and chromium layers may differ from 300 nm and 50 nm, respectively.

Figure 3:
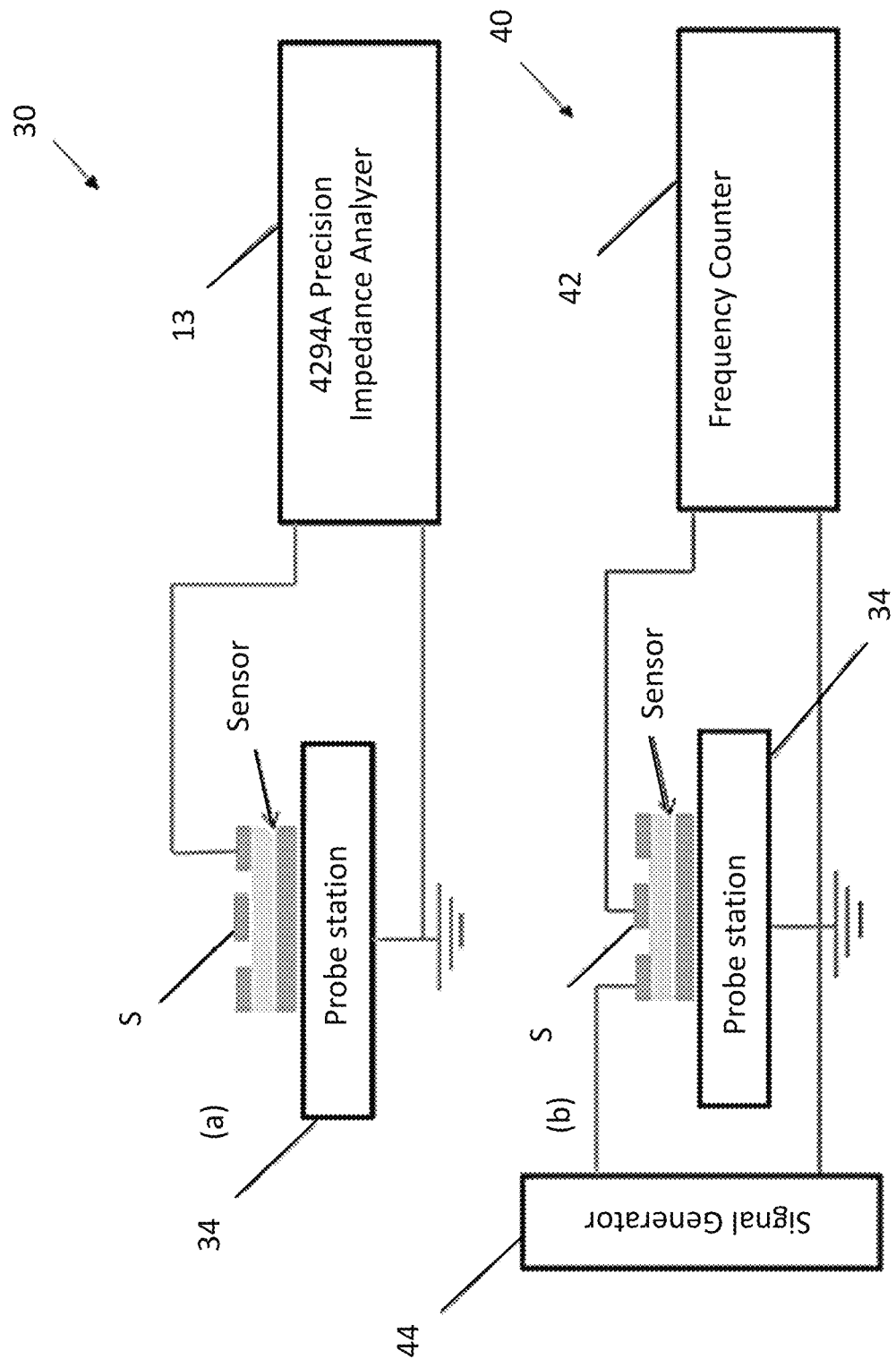
FIG. 3A shows a block diagram of a set-up for measurements of Q-factors, impedance, and dissipation factor versus frequency for embodiments of the sensor.
FIG. 3B shows a block diagram of a set-up for measurement of frequency shift versus time.

FIG. 3A is a block diagram of an experimental set up 30 for measuring Q-factor, impedance, and dissipation factor measurements using impedance analyzer 32 (e.g., 4294A Precision Impedance Analyzer) with the sensor S connected to probe station 34 (e.g., Signatone (S-1160 model). The sensor disks were mounted on the probe station 34 and connected with a coaxial cable to the impedance analyzer 32 in a series configuration. The electrical signal is applied at a resonant frequency of the top gold layer 14 while a ground terminal is connected to full bottom electrode 19. The measured parameters were Q-factors, impedance, frequency, capacitance, inductance, and dissipation factors in the frequencies between 1 MHz and 1.8 MHZ.

FIG. 3B is a block diagram of an experimental set up 40 for frequency shift measurement using a frequency counter 42, a signal generator 44, and a probe station 34. The disks were mounted on the top of the probe stations and the sinusoidal electrical signals were applied from the signal generator 44 to the ring electrode 12 while the full bottom electrode 19 was grounded. The frequency counter 42 was also connected to the disks using a coaxial cable, where the positive sinusoidal signals are extracted from the center dot electrode 13 while the bottom electrode was grounded. The measured parameters were frequencies shifts versus time.

Figure 4A:
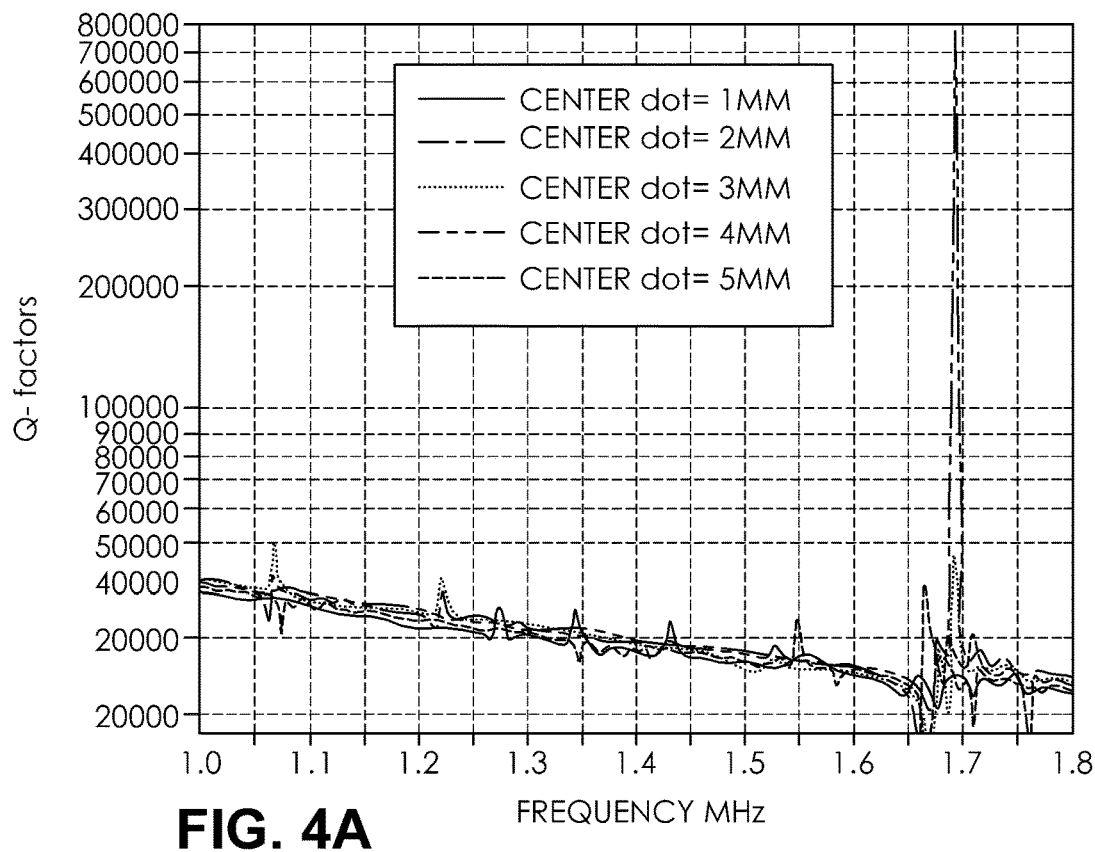
FIG. 4A is a plot of a curve which shows the measured Q-factors.

FIG. 4A is a plot of a curve which shows the measured Q-factors for varying the diameter of the center dot electrodes. As shown in the plot of FIG. 4A, a maximum Q-factor for the disk with a 2 mm center dot electrode was 785682 at 1.694 MHz. For the other disks with 1 mm, 3 mm, 4 mm, and 5 mm center dots, the measured Q-factors were between 20000 and 50000 at different frequencies between 1.0 MHz and 1.8 MHz. The Q-factors for the disk with a 3 mm center dot is 45000 at 1.694 MHz, 50000 at 1.06 MHz, and 40000 at 1.23 MHz. The Q-factor of the disk with 4 mm center dot is 40000 at 1.66 MHz, while that of the disk with 1 mm center dot is between 20000 and 40000 when the frequency is between 1.0 MHz and 1.8 MHz. When the frequencies are 1.0 MHz. 1.27 MHz, 1.35 MHz. and 1.44

MHz, the Q-factors for the 1 mm center dot disk are 40000, 37000, 36000 and 35000 respectively.

Figure 4B:
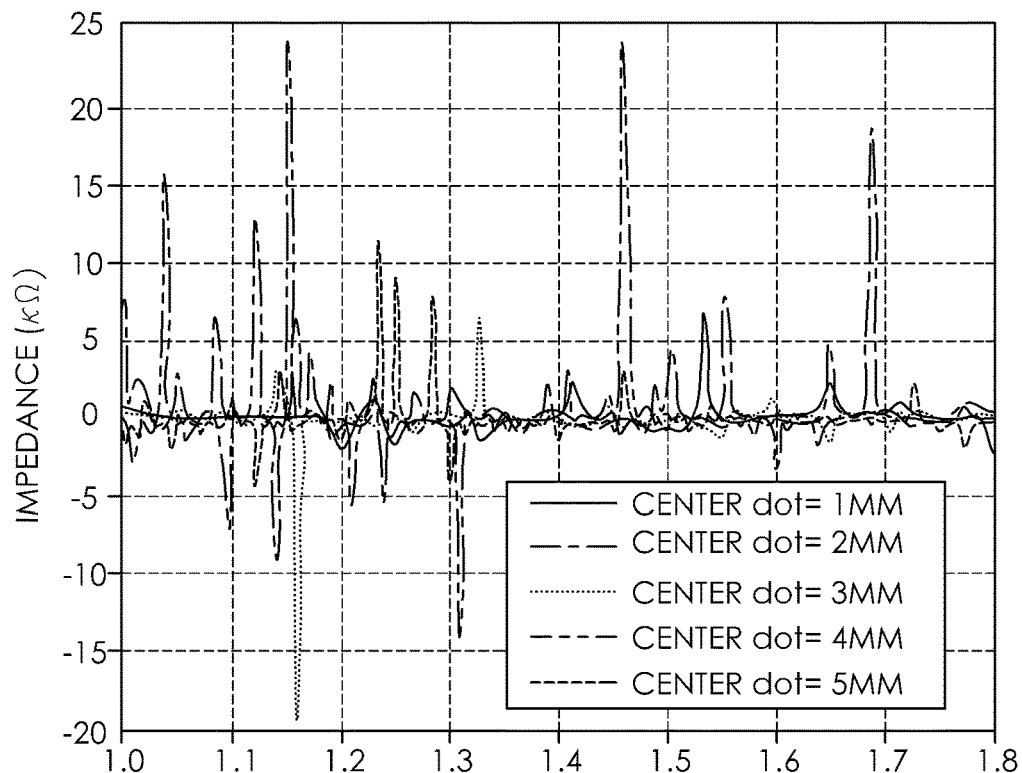
FIG. 4B is a plot of a curve which shows the measured impedance of five disks with varying center dot electrodes versus frequency.
Figure 5:
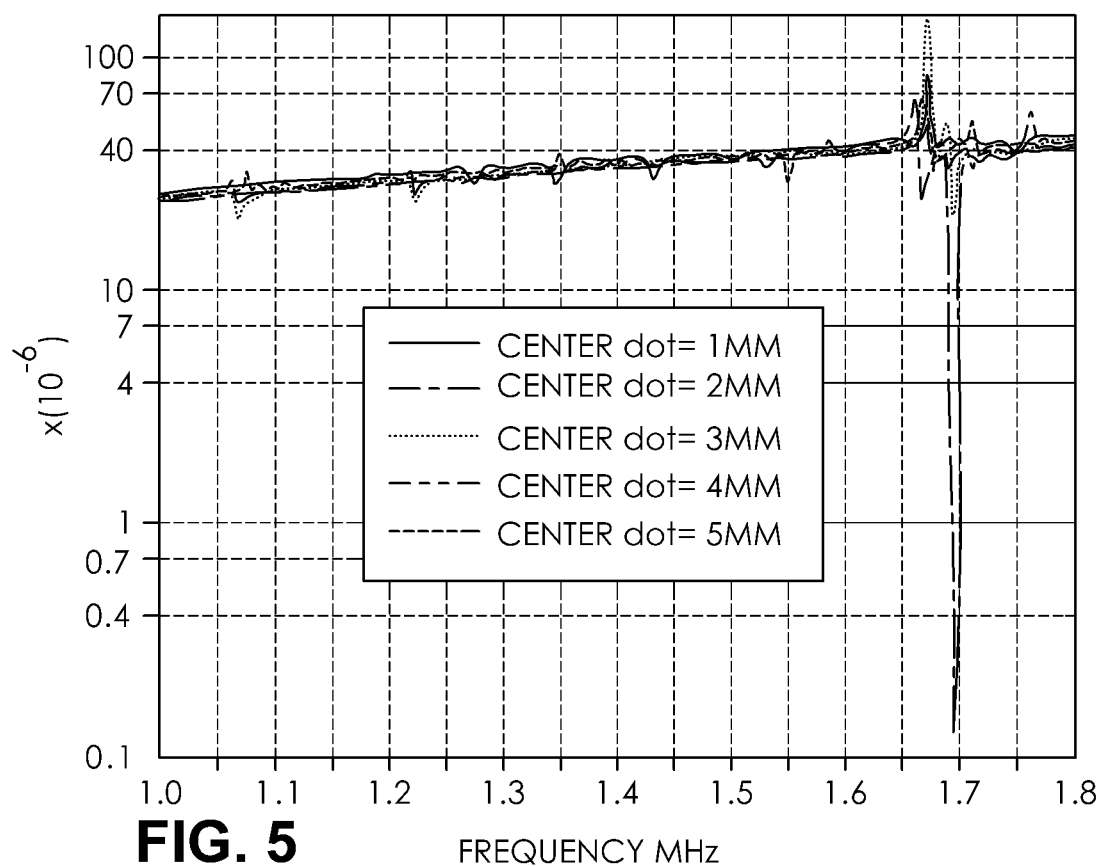
FIG. 5 is a plot of a curve which shows the measured D of five disks with varying center dot electrodes versus frequency.

FIG. 4B is a plot of a curve which shows the measured impedance of five disks versus frequency, where the five disks have 1 mm, 2 mm, 3 mm, 4 mm, and 5 mm center electrodes. The impedance measured when the frequency was between 1.35 MHz and 1.8 MHz are all positive, with the highest impedance being 22.5 kΩ for the disk with a 4 mm center dot and 17.5 kΩ for the disk with a 2 mm center dot. The disk with 4 mm center dot has 3 kΩ at 1.6 MHz and that with 3 mm has 1.5 kΩ at 1.65 MHz. The highest impedance observed between 1.0 MHz and 3.0 MHz is 24 kΩ for the disk with a 4 mm center dot and 19 kΩ for the disk with a 3 mm center dot when the frequency is 1.15 MHz. The curve which shows the measured dissipation factors of all five disks is shown in FIG. 5. The highest D was for the disk with the 2 mm center dot electrode, approximately $1.2*10^{-7}$, showing that this disk is 100 times more sensitive than the current practical D-QCM technology.

The obtained frequencies when measuring impedance and Q-factors were then used to calculate the mass sensitivity coefficients using Sauerbrey equation; $K=2*f^2/\sqrt{\rho\mu}=2.26*10^{-6}f^2$ Hz·cm$^2$/g, $\rho$ is the density of quartz crystal which is 2.648 g/cm$^3$, and $\mu$ is the shear modulus of quartz crystal which is $2.947*10^{11}$ g/cm·s$^2$. Since all the disks were measured at the same frequencies, the calculated mass sensitivity coefficient represents disks with 1 mm, 2 mm, 3 mm, 4 mm, and 5 mm center dots. The curve which shows the calculated mass sensitivity coefficients when the frequencies are from 1.0 MHz to 1.8 MHz is shown in FIG. 6.

Figure 7A:
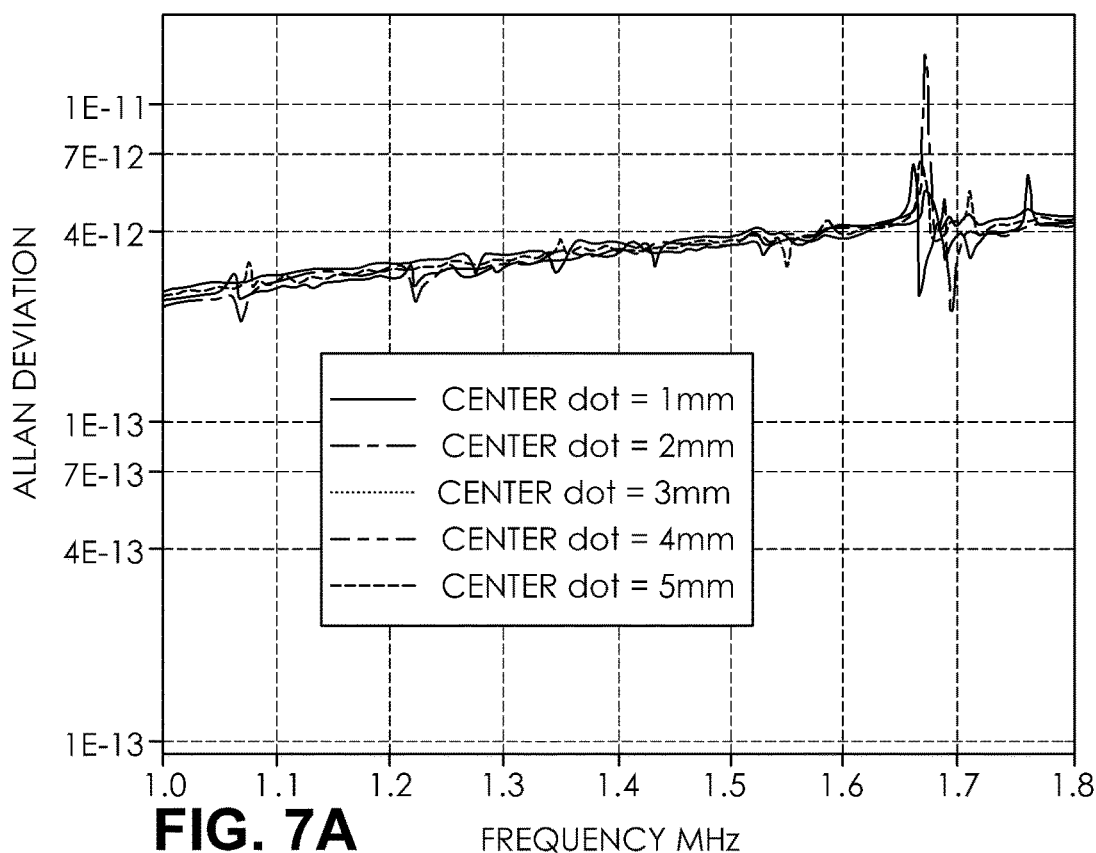
FIG. 7A is a plot of a curve showing calculated Allan deviation of five disks with varying center dot electrodes versus frequency.

The Allan deviation $\sigma(\tau)$ was calculated using the measured Q-factors from the expression $\sigma=10^{-7}/Q$, the obtained $\sigma(\tau)$ was then used to calculate the detection limit $\Delta f(\tau)$ using the equation, $\sigma(\tau)*f(\tau)=\Delta f(\tau)$, where $f(\tau)$ are the measured frequencies from 1.0 MHz to 1.8 MHz. The curve which shows $\sigma(\tau)$ is in FIG. 7A and the curve which shows detection limit $\Delta f(\tau)$ is shown in FIG. 7B.

Figure 6:
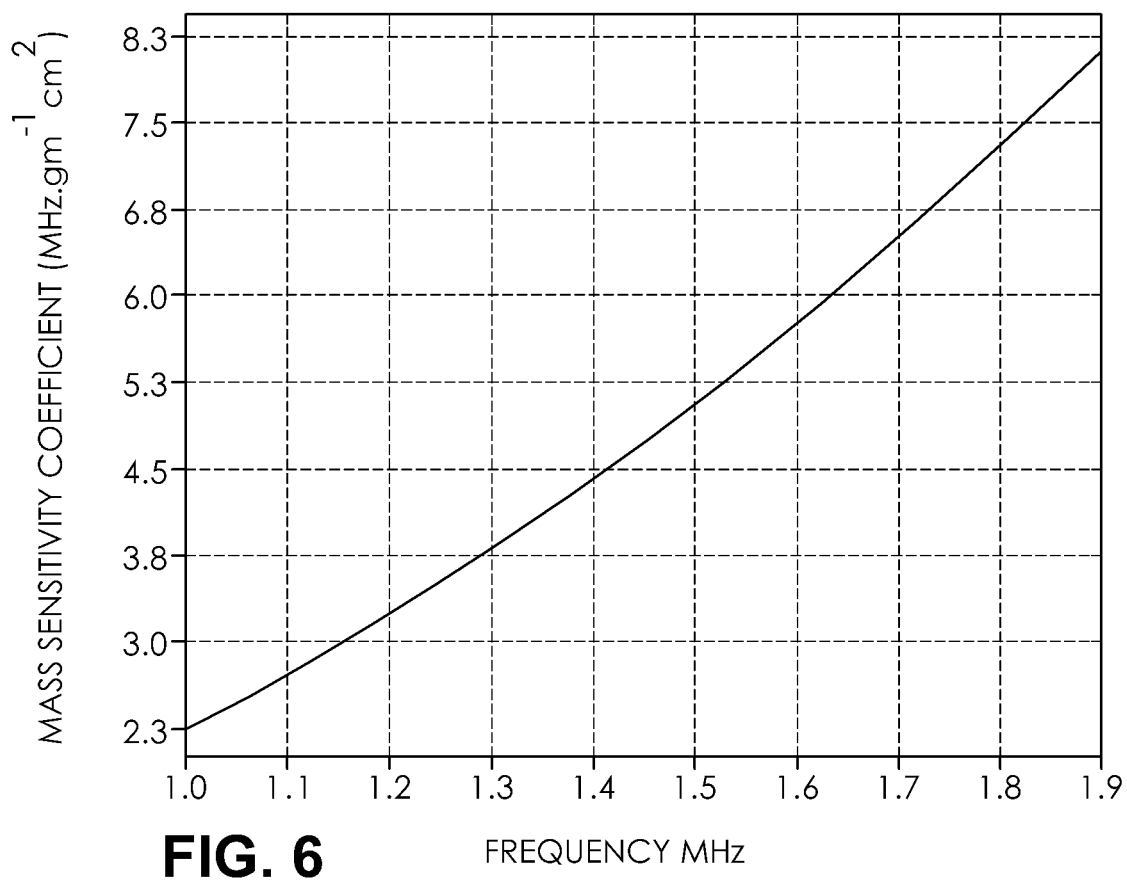
FIG. 6 is a plot of a curve which shows the calculated mass sensitivity coefficients of five disks with varying center dot electrodes versus frequency.
Figure 7B:
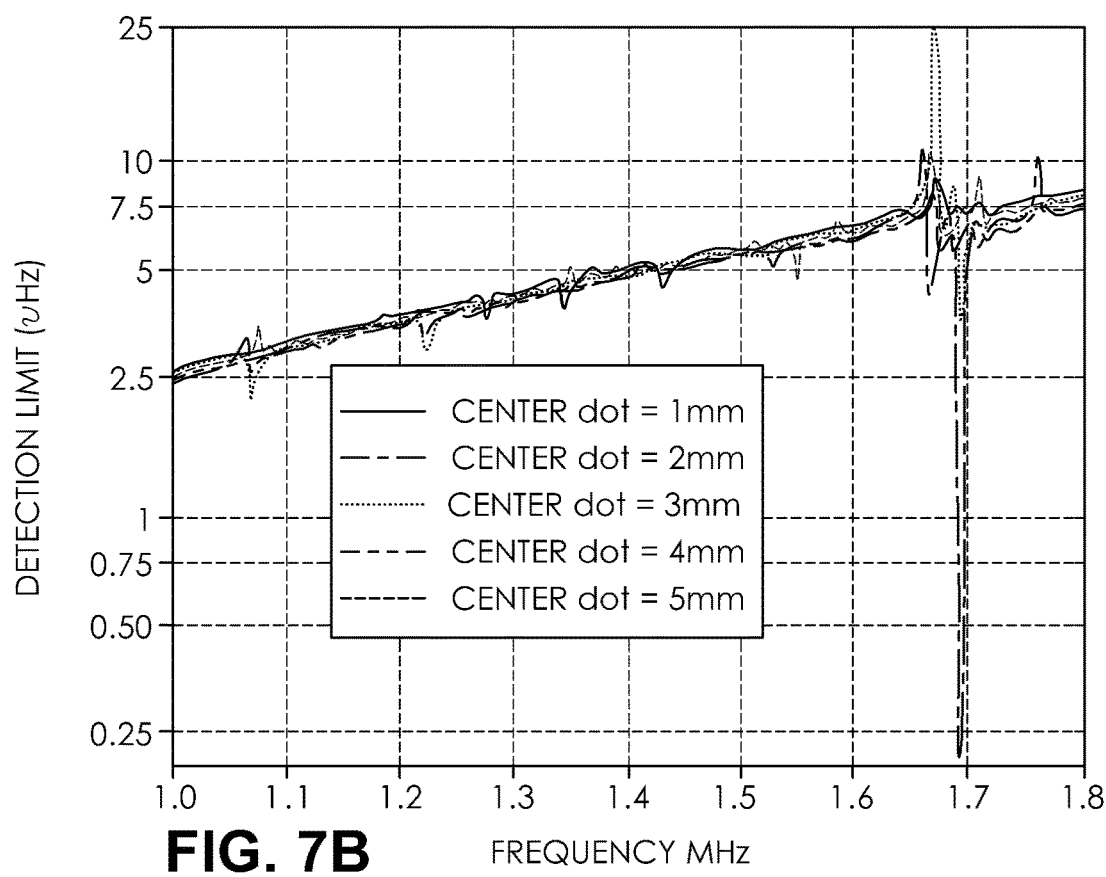
FIG. 7B is a plot of a curve showing the calculated detection limit of five disks with varying center dot electrodes versus frequency.
Figure 8:
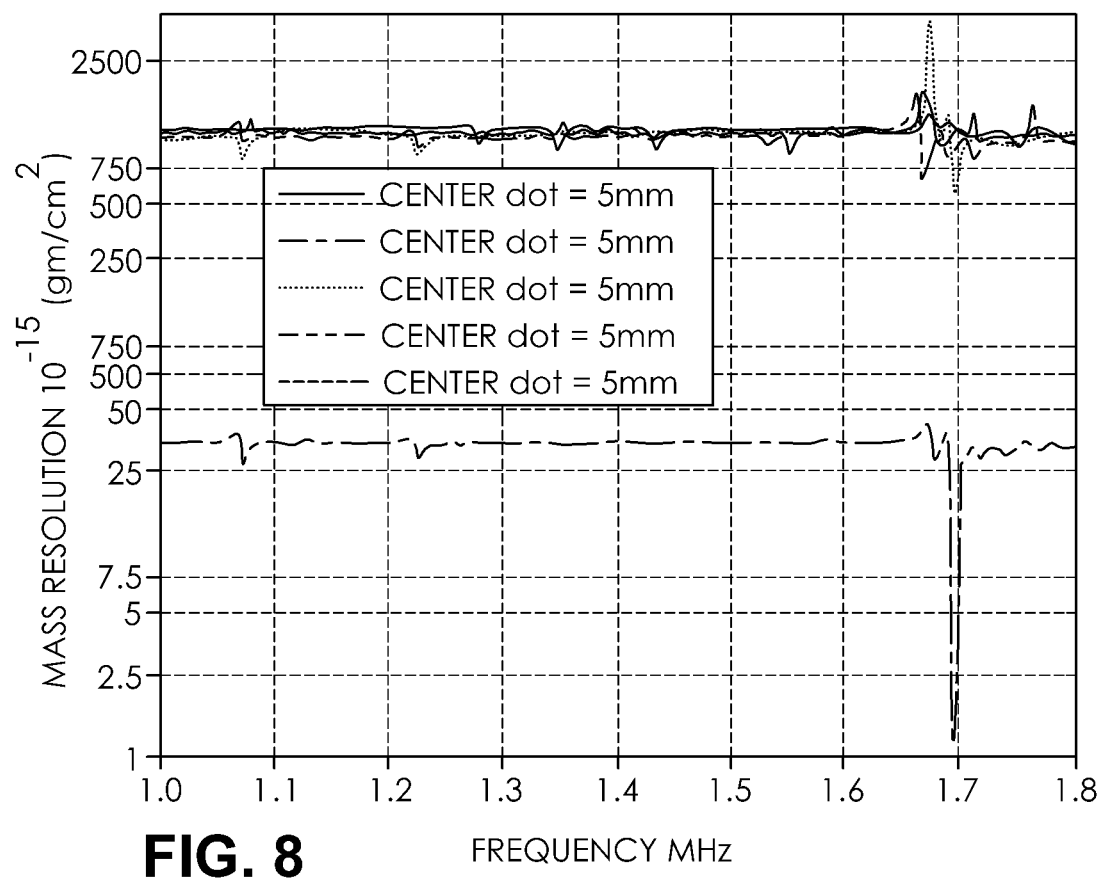
FIG. 8 is a plot of a curve showing the calculated mass resolution of five disks with varying center dot electrodes versus frequency.

The mass which can be detected on the surface of active center electrode area of each disk were calculated by taking the ratio of detection limit $\Delta f(\tau)$ in FIG. 7B to mass sensitivity coefficient (K) in FIG. 6. The curve of mass resolution per unit area of each disk is shown in FIG. 8, where the highest mass resolution is 1.23 fg/cm$^2$ at 1.694 MHz for the disk with a 2 mm center dot. When the frequencies are between 1.0 MHz and 1.66 MHz, the calculated mass resolution for the same disk is approximately 37 fg with a sharp peak at 1.07 MHz, and 27 fg with a sharp peak at 1.22 MHz. The disks with 1 mm, 3 mm, 4 mm, and 5 mm center dots have 1000 fg when the frequencies are between 1.0 MHz and 1.66 MHz. For the 3 mm center dot, the calculated mass resolution is 800 fg at 1.07 MHz and 560 fg at 1.694 MHz. The highest mass sensitivity is from the disk with a 2 mm center dot in the range from $3.76*10^{-14}$ to $1.23*10^{-15}$ g/cm$^2$ at 1.694 MHz.

Figure 9A:
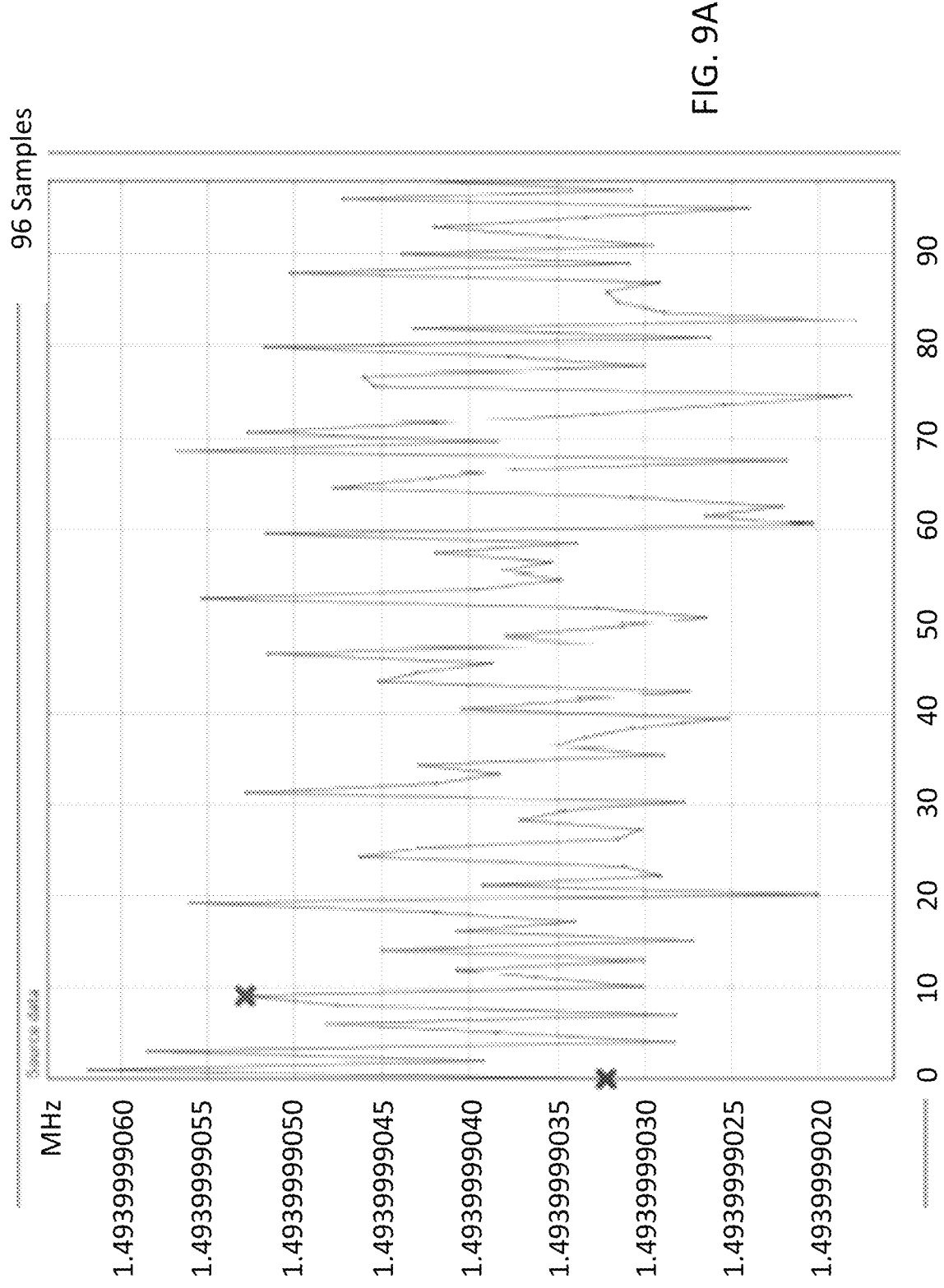
FIG. 9A is a plot of a curve showing the measured frequency shift ($\Delta f$) versus time for the disk with a 2 mm center dot electrode.
Figure 10:
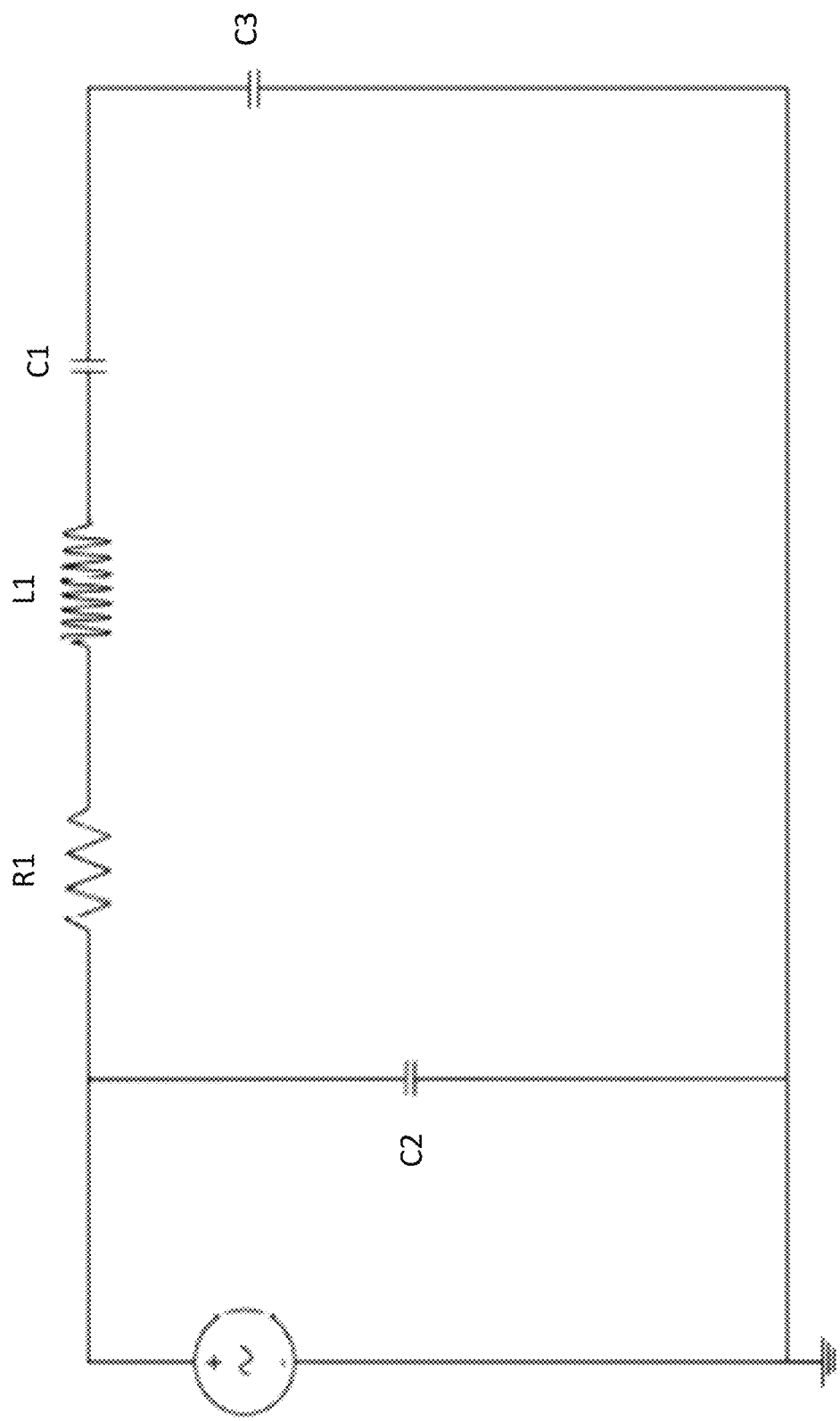
FIG. 10 is a schematic diagram of an equivalent circuit having an inductance (L1), capacitance (C1), resistance (R1), and static capacitance (C2 & C3)
Figure 11:
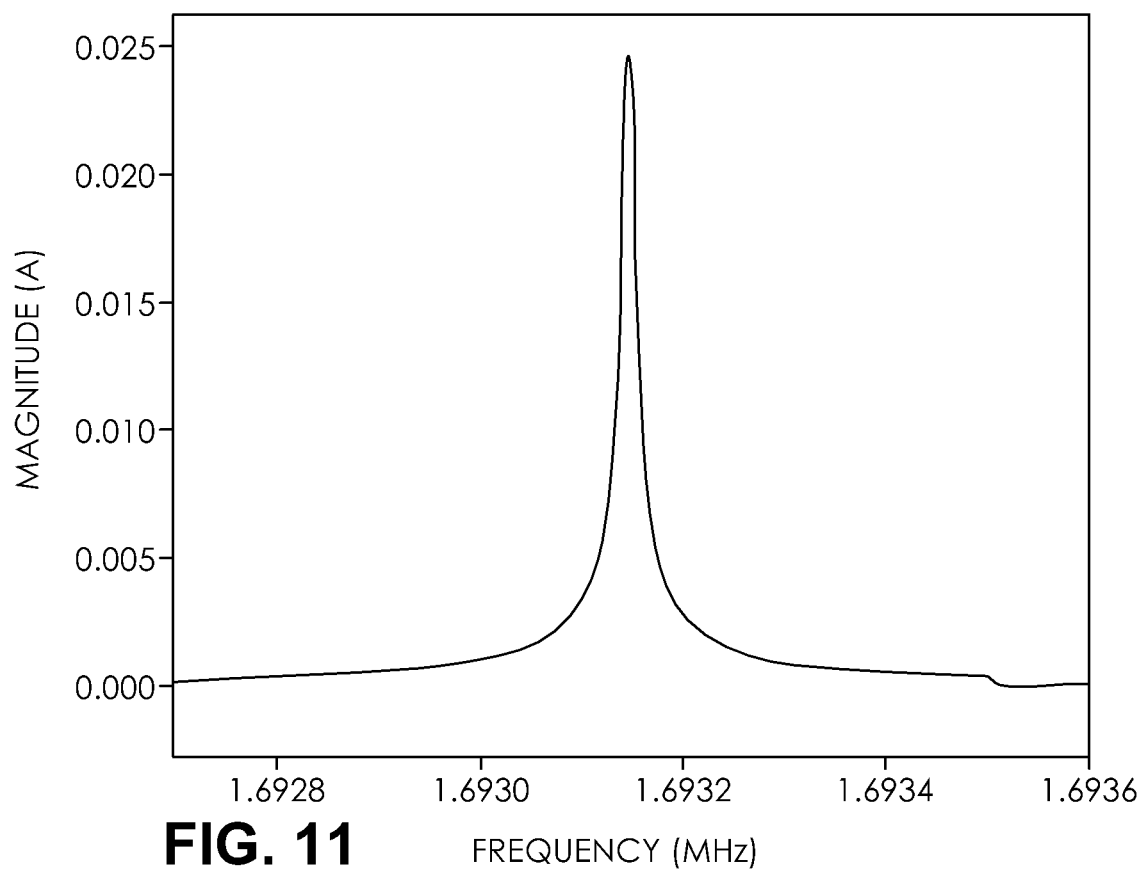
FIG. 11 is a plot of a curve which shows a simulated current (A) versus frequency (MHz) of the equivalent circuit at resonance (1.69 MHz)

FIG. 9 is a curve that shows the frequency shift obtained from the disk with a 2 mm center dot that was measured using a frequency counter for ten seconds. The ($\Delta f$) were captured using time view software, and the results are depicted in the left top corner of FIG. 9. The volume (V) of the Gold layer deposited on the quartz disk was then calculated using the equation $\pi r^2 t$ where t is $3*10^{-5}$ cm and r is 0.1 cm. The mass (m) of gold layer was calculated as $V*\rho=m$, where $\rho$ is the density of gold (19.3 g/cm$^3$). For this case, the mass of the gold layer is $1.8*10^{-5}$ g, and $\Delta m=(\Delta f/f)*m$; therefore, when $\Delta f=2*10^{-9}$ MHz, the $\Delta m=1.18*10^{-9}*1.8*10^{-5}$ g$=2*10^{-14}$ g. Upon frequency stabilization, by using electronic filters connected to the driving equivalent circuit, it was possible to measure fg/cm$^2$ as shown in the previous calculations at 1.694 MHz. Based on the measured high Q-factors it has been shown that it is possible to measure fg/cm$^2$ in the air, and was proved in the laboratory by measuring $\Delta f$ which is equivalent to $2*10^{-14}$ g/cm$^2$. In a vacuum, this disk could measure mass up to ag/cm$^2$. The measured electrical counterpart parameters of the disk with 2 mm center electrode are presented in the electrical equivalent circuitry parameters in FIG. 10, which shows series capacitance, inductance, and resistance of the disk. The results showing the simulated currents using multisim circuit design software is depicted in FIG. 11.

As it has been shown, the most sensitive sensor is the disk with a 2 mm center dot electrode. The disk with the 2 mm center dot is capable of measuring mass from $3.76*10-14$ g/cm$^2$ to $1.23*10^{-15}$ g/cm$^2$. While single-walled carbon nanotube SWNT/AT-cut quartz is reported to have a mass sensitivity of $100*10^{-15}$ g/cm$^2$ in a vacuum, embodiments of the inventive disk with a 2 mm center dot is 100 times more sensitive. In addition, all four disks with 1 mm, 3 mm, 4 mm, and 5 mm center dot electrodes could measure fg in a vacuum if tested in the same environments as claimed in a micromachined SWNT/AT-cut quartz wafer when tested at 48.535731 MHz. Embodiments of the invented disks are more than 10,000 times more sensitive than any existing sensor when tested in a vacuum.

Embodiments of the inventive sensors when integrated with ultrasonic acoustic force/crystal microchannels doped antibody or microfluidic separation techniques, may be arranged in an array with varieties of digital signal processing. Furthermore, embodiments of the inventive disks may have sensor surfaces beyond Au with gold nanoparticles functionalized with anti-troponin, anti-body, and antigen configurations.

EXAMPLES

Example 1

Figure 12:
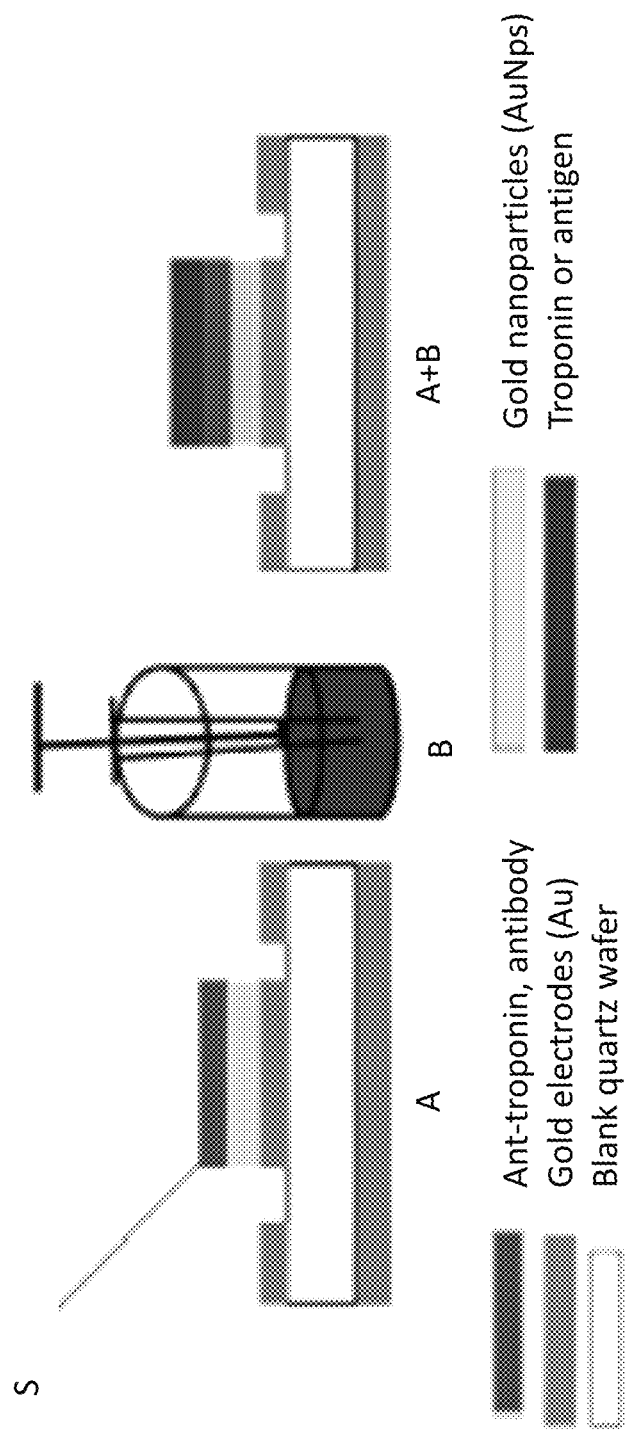
FIG. 12 is a block diagram of a set-up for blood serum collection for verification of fg measurements in air using anti-troponin/gold nanoparticles functionalized on a 2 mm center dot electrode.

FIG. 12 illustrates a set-up for blood/air ultrasonic acoustic forces/crystal microchannel/microfluidic separation to isolate specific antigen, a virus, a cell, or a troponin molecule for the detection and verification of fg measurements in the air/blood, using an ultra-sensitive disk with anti-troponin/gold or antibody/gold nanoparticles functionalized on the 2 mm center dot electrode as described in FIGS. 1 and 2. Embodiments of the inventive sensors can be used not only as biosensors for the early detection of troponin for myocardial infraction (MI) before it happens; but also, as an immunoassay to detect airborne pathogens before infection. The first part of this technology includes an external test immunoassay/special crystal window doped with an antibody which contains an isolated virus, troponin, or bacteria from the whole blood or the ambient air as shown in FIG. 12.

Example 2

FIG. 13 illustrates a flow chart 50 which shows blood or air flow fed into the microfluidic driven by ultrasonic acoustic standing wave attached to a sensor with antibody and gold, functionalized on QCM mass sensor. The method 50 begins with forming a sample of blood mixed with saline solution or a sample of ambient air (Block 52), and feeding the sample into a microfluidic-controlled by ultrasonic acoustic forces (Block 54) that separates the supplied whole blood sample into suspended particles of antigens, antibodies, electrolytes, cells, bacteria and troponins; or the sampled air into antigens (Block 56). The separated whole blood sample or the sample air antigens are supplied to a reflector via crystal assay microchannels/microfluidic (Block 58) to apply the samples to an embodiment of the QCM mass sensor, where the QCM sensor S is coated with an antibody or anti-troponin (Block 60).

The components of the microfluidic delivery system illustratively include; special crystal assay windows/channels doped with antibodies, micro pumps, micro valves, micro volumes, ultrasonic acoustic forces and a reflector, while the sensing components illustratively include biomarkers and special assay formats with gold nanoparticles on QCM. Successfully interfacing the microfluidic delivery system with QCM mass sensor makes it possible to develop cost-effective diagnostic POC systems.

Example 3

Figure 14:
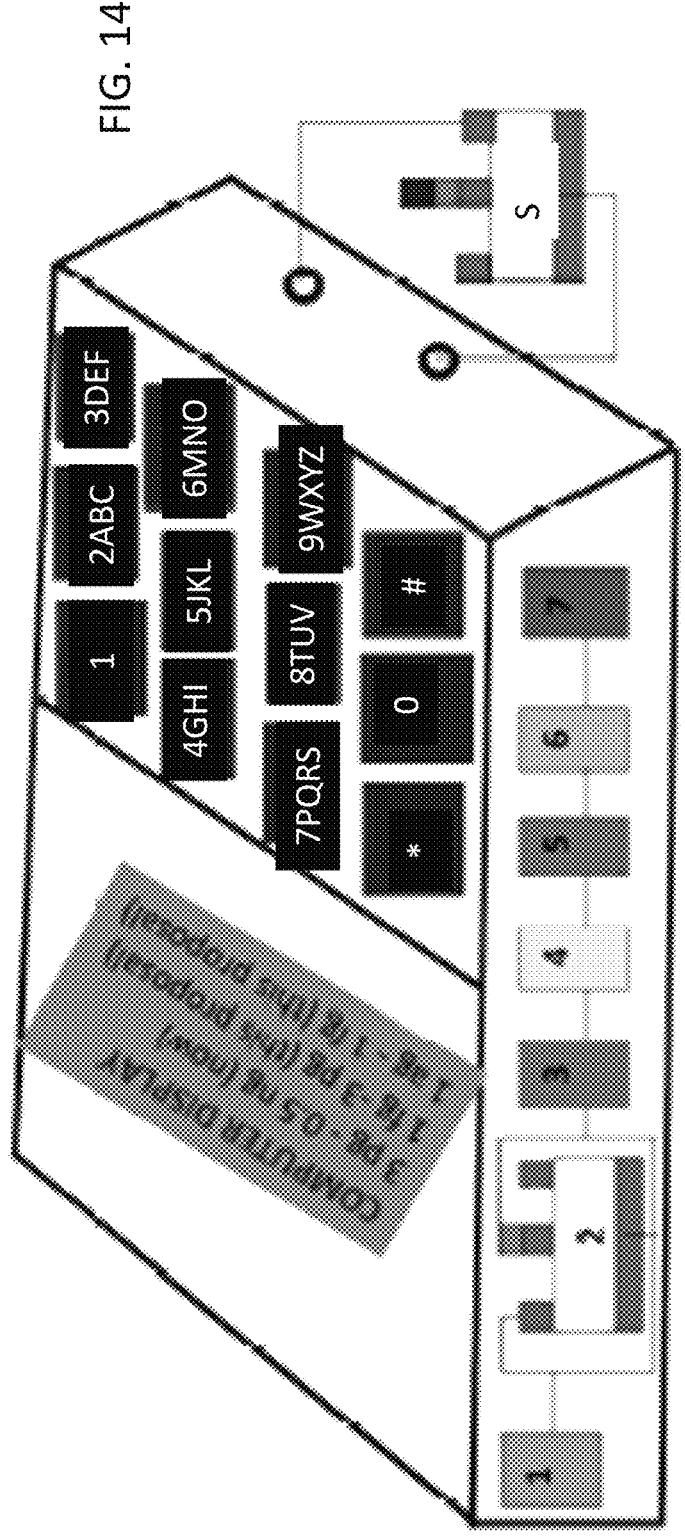
FIG. 14 shows a schematic drawing of a portable ultrasensitive troponin meter employing the use of sensors disks in accordance with embodiments of the invention.

FIG. 14 illustrates a compact "Portable Ultrasensitive Troponin Meter" which includes a built-in and a reference immunoassays. The meter is designed for use in home settings, hospitals, and home care facilities; where the patients may use the available glucometer's lancing device to withdraw 1 mm$^3$ of their own blood on the fingertip and add the withdrawn blood on an external or reference immunoassay, which is then tested for a troponin level using the "Ultrasensitive Troponin Meter" with built-in immunoassay.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.
(K).

The invention claimed is:

1. A sensor comprising:
a quartz substrate with a top side and a bottom side, said quartz substrate having a diameter;
a center electrode centered on the top side of said quartz substrate, said center electrode having a diameter that is smaller than the diameter of said quartz substrate;
a ring electrode on the top side of said quartz substrate surrounding said center electrode, said ring electrode having an outer diameter that is equal to the diameter of said quartz substrate;
a gap between said ring electrode and said center electrode; and
a bottom electrode fully coating the bottom side of said quartz substrate.

2. The sensor of claim 1 wherein said quartz substrate is a round disk.

3. The sensor of claim 1 wherein the diameter of said quartz substrate is 10 mm.

4. The sensor of claim 1 wherein said center electrode and said ring electrode further comprises a layer of chromium adhesive applied to the top side of said quartz substrate and a gold layer applied to the chromium adhesive layer.

5. The sensor of claim 4 wherein said layer of chromium adhesive is 50 nm.

6. The sensor of claim 4 wherein said gold layer is 300 nm.

7. The sensor of claim 1 wherein said bottom electrode further comprises a bottom side layer of chromium adhesive applied to the bottom side of said quartz substrate and a bottom side gold layer applied to the bottom chromium adhesive layer.

8. The sensor of claim 1 wherein the diameter of said center electrode is one of 1 mm, 2 mm, 3 mm, 4 mm, or 5 mm, the width of the corresponding gap is 2.5 mm, 2 mm, 1.5 mm, 1 mm, or 0.5 mm, respectively.

9. The sensor of claim 1 wherein said center electrode has a first layer of cTnI and a subsequent second layer of cTnT assay applied, where the first and second layers are able to detect troponins in a femtogram regime.

10. A portable device for detection of airborne pathogens in ambient air before infection, and detection of a troponins level in blood serum before the occurrence of the acute myocardial infraction (AMI) or stroke in a subject, wherein said portable device uses the sensor of claim 1.

11. The portable sensor of claim 10 wherein said center electrode and ring electrode are built-in immunoassays with anti-troponin, antibody, and antigen; whereby, detection is determined by introducing external immunoassay of troponin, antibody, antigen, functionalized on said built-in immunoassay.

12. The portable device of claim 10 further comprising wireless medical diagnostic sensors to connect with wireless networks to connect patients in home settings to central laboratories or doctors' office to access patients' health condition in real time.

13. A method of using the sensor of claim 1 comprising:
forming a sample of blood mixed with a saline solution or a sample of ambient air;
feeding the sample into a microfluidic/crystal microchannels doped antibody-controlled by ultrasonic acoustic forces to separate the supplied whole blood sample into suspended particles of antigens, antibodies, electrolytes, cells, bacteria and troponins, or the sampled air into antigens;
coating the sensor with an antibody or anti-troponin; and
supplying the separated whole blood sample or the sample air antigens to a reflector to apply the samples to the sensor.

14. The method of claim 13 wherein the sensor is an ultrasensitive high Q-factor AT-cut quartz crystal microbalance (QCM) mass sensor.

* * * * *